(12) United States Patent
Brone et al.

(10) Patent No.: US 7,240,575 B2
(45) Date of Patent: Jul. 10, 2007

(54) METHOD AND APPARATUS FOR SEGREGATION TESTING OF PARTICULATE SOLIDS

(75) Inventors: Dean Lance Brone, Ann Arbor, MI (US); Scott A. Clement, Atascadero, CA (US); Bruno Caspar Hancock, North Stonington, CT (US); David Bruce Hedden, Ann Arbor, MI (US); Michael A. McCall, Atascadero, CA (US); James K. Prescott, Shrewsbury, MA (US); Thomas G. Troxel, San Luis Obispo, CA (US)

(73) Assignee: Jenike & Johanson, Inc., Westford, MA (US)

( * ) Notice: Subject to any disclaimer, the term of this patent is extended or adjusted under 35 U.S.C. 154(b) by 60 days.

(21) Appl. No.: 11/177,615

(22) Filed: Jul. 7, 2005

(65) Prior Publication Data

US 2007/0006671 A1 Jan. 11, 2007

(51) Int. Cl.
*G01N 33/00* (2006.01)
(52) U.S. Cl. ........................................................ 73/866
(58) Field of Classification Search ................... 73/866
See application file for complete search history.

(56) References Cited

U.S. PATENT DOCUMENTS 6,487,921 B1 12/2002 Prescott et al.

OTHER PUBLICATIONS

ASTM International, "Standard Practice for Measuring Fluidization Segregation Tendencies of Powders," Designation: D 6941-03.
Hullin, Lu, et al., "Size segregation of binary mixture of solids in bubbling fluidized beds," *Powder Technology*, vol. 134:86-97 (2003).
Hoffmann, A.C., et al., "Segregation in a fluidised powder of a continuous size distribution," *Powder Technology*, vol. 66:119-126 (1991).

*Primary Examiner*—Robert Raevis
(74) *Attorney, Agent, or Firm*—Lahive & Cockfield, LLP

(57) ABSTRACT

A bed of particulate solids is fluidized in a test chamber to yield multiple test samples for subsequent evaluation of segregation effects. A controlled stream of gas enters the chamber in a series of flow rate cycles each progressively increasing to a maximum rate of gas flow and then decreasing, the maximum rate increasing for successive cycles. An indicating function is formed from measurements of corresponding rates of gas flow and pressure across the bed. Upon termination of the fluidization, multiple samples are sequentially extracted from a single space at the bottom of the test chamber.

9 Claims, 9 Drawing Sheets

METHOD AND APPARATUS FOR SEGREGATION TESTING OF PARTICULATE SOLIDS

BACKGROUND OF THE INVENTION

This invention relates to a method and apparatus useful for testing powders and other particulate bulk solids with the object of evaluating their segregation tendencies when fluidized under industrial conditions.

To facilitate the industrial processing of powders and other particulate solids it is common practice to blow air or other gas into the body of the material. At a sufficient gas flow rate this results in fluidization, a state in which the solids exhibit fluid-like properties. Fluidization may also occur unintentionally, for example during transfer of powder from a blender to a bin, when air flow through the material may fluidize or partially fluidize the material.

However, fluidization is the driving force for a segregation mechanism that alters the uniformity of the properties of the solids in different parts of the body, notably the particle size distribution, but also other properties including for example particle shape, chemical assay, bulk density, color, and solubility. Nonuniformity of these properties generally degrades the quality of the industrial product.

To obtain useful data on the tendency of a particular body of solids to undergo significant segregation when fluidized under industrial conditions, simulation test practices have been devised. These simulate the industrial conditions using a quantity of the solids in a test chamber, employing an accurately repeatable fluidization test procedure. At the conclusion of a test, multiple samples are taken from different parts of the test chamber and subjected to separate assays and analyses of the properties of interest. These results for a new material may be compared with the results for other solids having known segregation properties when similarly tested in the same apparatus and with the same fluidizing test procedure. This comparison provides an indication of potential of the new material to segregate by fluidization in a given industrial application.

The tester can also be used simply to determine the suitability of a new material to fluidize in an industrial application, irrespective of segregation potential or concerns.

The objects of the present invention are directed to improved test apparatus and procedures. The resulting samples may be evaluated using presently existing or future techniques.

A standard practice for measuring fluidization segregation tendencies of powders is described by ASTM International under Designation D6941-03. A suitable apparatus for the purpose is described in U.S. Pat. No. 6,487,921. A vertical columnar test chamber is filled with a bed of the solids, subjected to a fluidization procedure and adapted for removal of samples from several vertical levels of the chamber after completion of the procedure. During the procedure air or other gas is forced into the bottom of the chamber under pressure, and the gas flow rate is measured and increased to a "high flow rate" at which the bed is observed to be fluidized. The flow rate is then reduced to a "low flow rate" at which a minimum level of fluidization is noted, then held at or near the low flow rate for a predetermined "hold time," and finally reduced to zero. The fluidization of the bed allows or may cause segregation of the material. For example, in powders of mixed particle sizes, segregation causes the lighter, finer particles to increase in concentration towards the top, and the coarser, heavier particles to increase in concentration at the bottom.

In practice, the existing standard practice and its variations have a number of drawbacks. For example, it is frequently necessary to run two tests for each material, a first or characterizing test to determine the appropriate high and low flow rates, and a second or actual test to produce the samples for analysis.

The existing test procedure is influenced by subjective factors varying with the individual performing the test, including observation of the material behavior such as formation of bubbles or turbulence at various levels in the material and expansion or lifting of the bed of material, and control of the rate of change in the flow rate. Thus different persons can produce different test conditions and cause inaccurate, nonrepeatable test results.

The existing standard test procedure typically yields individual samples of substantial volume which, although suitable for certain types of analysis, are often too large for some other common analytical methods. As a result, time consuming sub-sampling, sample splitting or riffling procedures are needed to obtain validly representative smaller quantities for analysis. Sub-sampling can also lead to errors and material loss.

The existing standard test has proven ineffective for certain materials that do not fluidize easily using the prescribed time and flow rate profile.

The existing standard test procedure typically consumes as much as 85 ml of material not only for the first or characterizing test, but also another 85 ml of material for the second or actual test. This is often more material than the quantity available during early stages of development of a particulate solid material, for example a pharmaceutical formulation. Attempts to reduce the size of the current test chamber, while employing the same fluidization profile described in the ASTM method, are ineffective for cohesive materials, since the wall effects, i.e. the total friction along the walls of the chamber relative to the weight of the material, are more pronounced.

BRIEF SUMMARY OF THE INVENTION

With the object of overcoming the above and other drawbacks, the features of this invention include a flow rate cycling or ramp-up method of controlling the gas flow rate for the achievement of fluidization in the test chamber. This method permits the fluidization of materials that do not fluidize easily, and reduces the likelihood of channeling of the gas, cohesive effects, and entraining of particles in the gas stream.

According to another feature of the invention, the flow rate cycling method is employed in conjunction with the monitoring and recording of the gas pressure at the inlet to the test chamber. This permits observation of the functional relationship between the gas flow rate and the inlet pressure as an indication of fluidization conditions in the test material.

In particular, a preliminary test of the apparatus may be conducted with the test chamber empty to measure and record the background pressure drop measured at the inlet to the chamber as a function of the rate of gas flow. This pressure drop is the result of friction and turbulence effects created within the gas flow passages, apart from the test material. In the subsequent tests with material in the test chamber, the appropriate background pressure drop may be subtracted from the measured pressure to yield the net pressure drop through and due to the bed of material under test.

An indicating function is produced and may be plotted to show values of the net pressure drop as a function of the gas flow rate. Observation of this function permits less subjective evaluation of the state of fluidization and subsequent control of the test, as hereinafter more particularly described.

A feature of the invention is an improved method of extracting samples from the test chamber. The samples at a plurality of vertical levels are sequentially removed from the bottom of the chamber. The samples are of small size as compared, for example, to those obtained with the apparatus of U.S. Pat. No. 6,487,921, and are preferably equal in volume to that required for assays or other methods of analysis. This eliminates the need to sub-sample or subdivide the sample by riffling, both of which take additional time and can result in errors and material losses.

Another feature of the invention is that it enables the use of a test chamber of smaller size than the chamber used in the existing apparatus, requiring as little as 19 ml per test, for example, while being effective even for more cohesive materials. This reduces cost and material waste, and may allow testing in some cases where larger samples cannot be provided.

As a consequence of the foregoing and other features hereinafter described, the invention uses less test material, provides increased sensitivity to and resolution of segregation that has occurred, is more likely to reach full fluidization of the test material, reduces the subjectivity of the observations and control of test conditions, and produces samples of a size that can be used directly in common assay methods.

DETAILED DESCRIPTION

Figure 1:
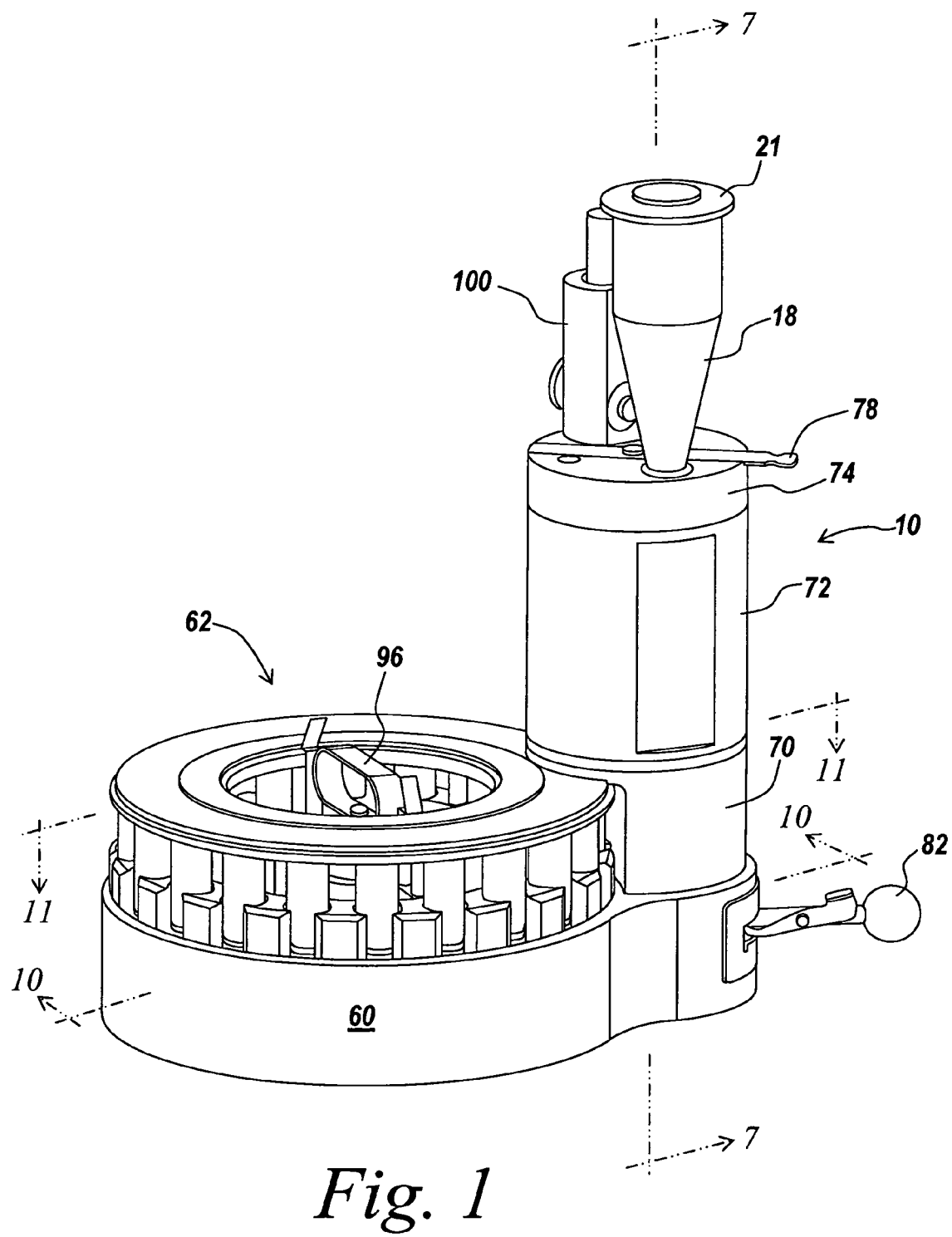
FIG. 1 is a view in perspective of the tester.
Figures 2, 3:
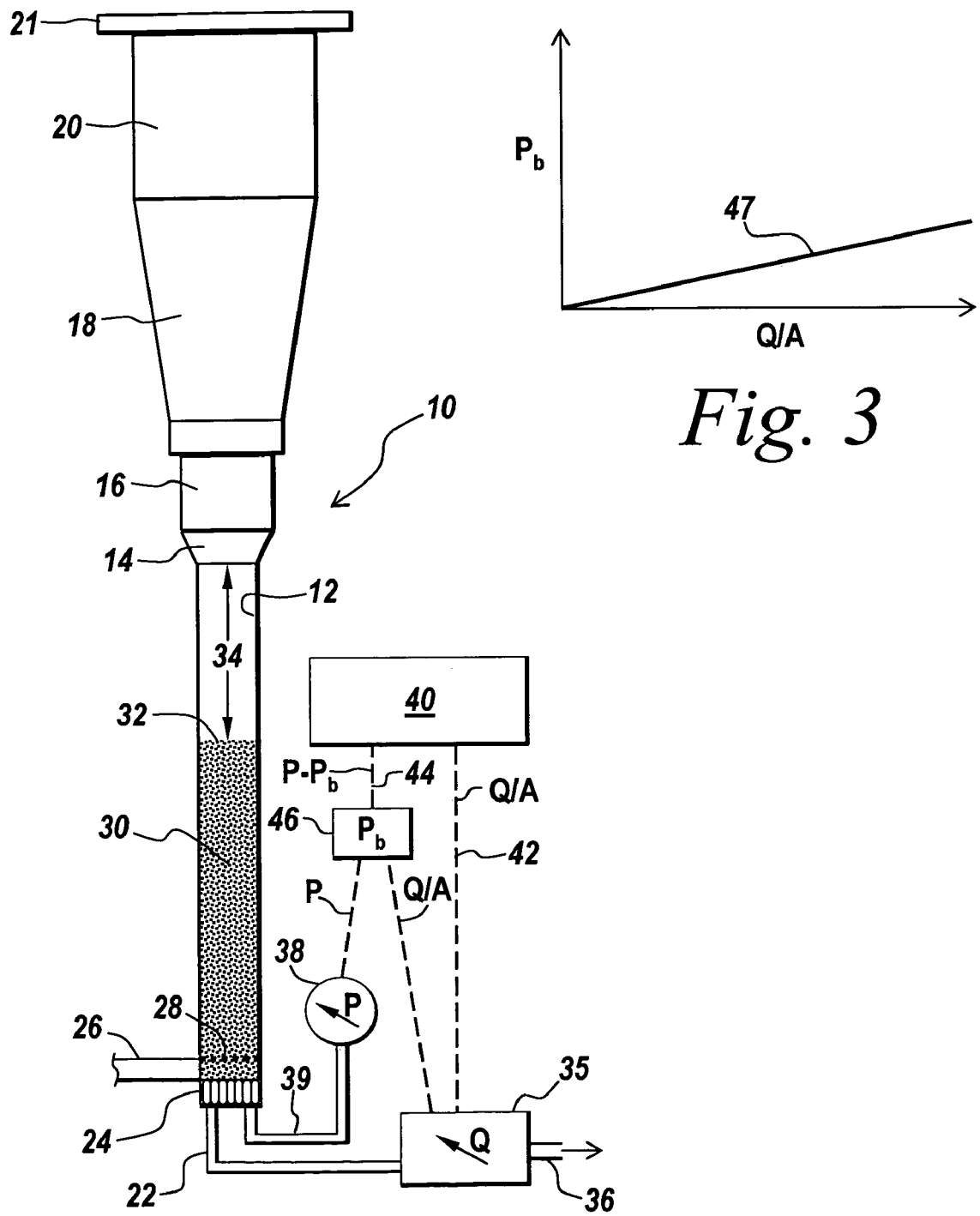
FIG. 2 is a schematic drawing of the testing apparatus for purposes of explanation.
FIG. 3 is a plot showing the background pressure drop stored in a memory as a function of the rate of gas flow.

FIG. 1 is a general view of the preferred form of tester and FIG. 2 schematically shows the tester connected with added components to form the complete testing apparatus.

A test column indicated generally at 10 forms a vertical cylindrical test chamber 12, a conical expansion section 14 useful for breaking up conveyed plugs of material, a vertical section 16, an elutriation chamber 18 for separation of gas from the material, a dust filter 20, and a cap 21.

A fluidizing gas tube 22 is connected to a diffuser 24 of sintered metal or the like located at the bottom of the chamber 12 for injecting gas into the material uniformly over the cross sectional area "A" of the chamber. A sampling disk 26 is located preferably immediately above the diffuser with a recess 28 therein removably located below the chamber 12 and containing the lowermost layer of a bed 30 of test material such as powder or the like. The disk 26 has multiple recesses arranged for sequential movement into the space occupied by the recess 28 for successively removing layers of the material in the bed after completion of a test, as hereinafter described in connection with FIGS. 10 and 11.

Typically, the bed 30 is filled to a level 32, allowing additional space 34 for bed expansion as hereinafter described. The diverging section 14 is provided for plug breaking as needed in conjunction with the testing of certain materials.

A flow controller 35 has a connection 36 to a source of fluidizing gas under pressure (not shown), for example air, nitrogen or another gas similar to that employed under expected industrial conditions for the material under test. The controller 35 may be a conventional device for indicating and controlling the rate of gas flow "Q," namely the volume rate of gas flow in the inlet tube 22.

A pressure sensor 38 is connected to the diffuser 24 by a tube 39 and indicates the pressure "P" at the inlet to the diffuser 24.

Figure 5:
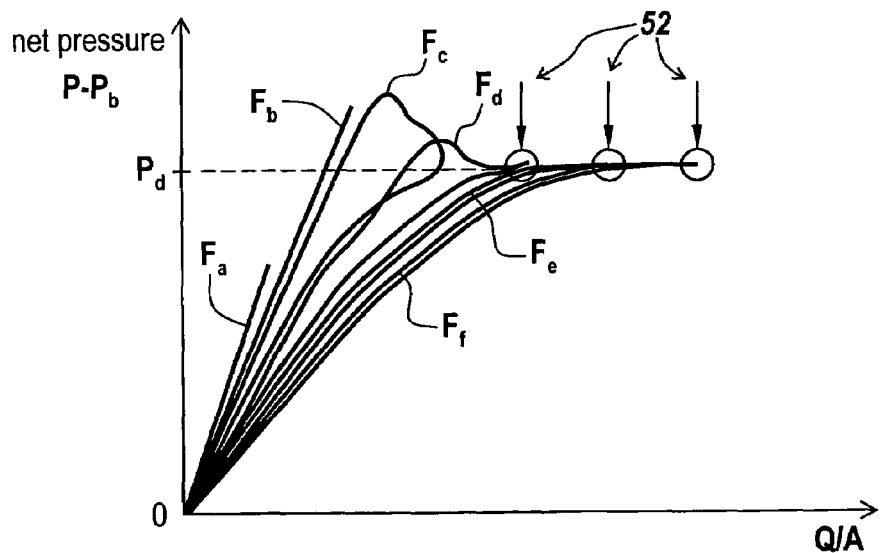
FIG. 5 is a plot of the response of the net pressure to the cycling flow rate produced during an illustrative test of a particular material, idealized for purposes of explanation.

An indicating function generator 40 is provided with an input connection 42 for receiving a value Q/A, "A" being the cross sectional area of the bed 30. A second input 44 receives a value P-$P_b$, whereby the generator 40 produces a function profile of its inputs for observation of a test. FIG. 5 illustrates such functions.

The quantity "$P_b$" is a background pressure drop and is a function of "Q" as determined in a preliminary test run as next described. This function is retained in a memory 46 having means to subtract the appropriate background pressure drop from each measured level of "P" during a test.

To determine the background pressure drop function, a preliminary test run is conducted with no material in the test chamber. The flow rate is increased from zero to the maximum value expected during a test, and corresponding levels of $P_b$ are recorded in the memory 46, idealized levels being represented in FIG. 3 by a straight line 47.

Figure 4:
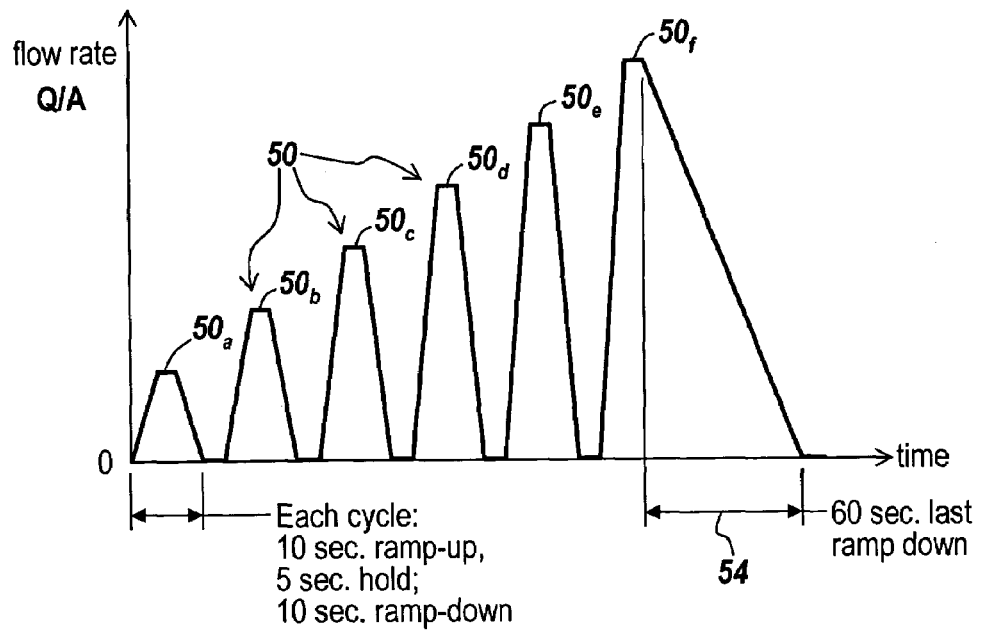
FIG. 4 is a plot or profile of the gas flow rate against time during a test according to the invention, illustrating the flow rate cycling and ramp-up method of the invention.

The test chamber is then loaded with a bed 30 of test material up to the level 32 allowing space for expansion. In the method of this invention, the controller 35 is adapted to control the flow rate Q/A in cycles 50 as shown in FIG. 4, each cycle being of controllable duration and comprising a ramp-up subperiod to a maximum value, a hold subperiod at the maximum value and a ramp-down subperiod to zero. The ramp-up, hold and ramp-down subperiods are of controllable duration. Pauses of controllable duration are preferably provided between successive cycles. The duration of each of the sub-periods in seconds as shown in FIG. 4 is a presently preferred value, and in practice it is selected by the user.

The maximum flow rate increases in magnitude from each cycle to the next succeeding cycle by the same predetermined increment or a changed increment determined by observation during the test.

The initial cycle $50_a$ reaches a maximum flow rate less than that which causes fluidization of the particular material.

As shown in FIG. 5, the corresponding plot produced in the cycle $50_a$ by the generator 40 is represented by a function $F_a$ showing that the net pressure rises linearly with respect to the flow rate, and descends linearly to zero on the same line, thus being "path independent."

A second cycle $50_b$ generates a second linear function $F_b$, indicating that the maximum flow rate in this cycle has not yet achieved fluidization of the material.

A third cycle $50_c$ reaches a flow rate exceeding that which initiates fluidization of the material. As shown by the resulting curve $F_c$, expansion of the fluidized bed begins and causes decreasing bulk density with a consequent drop in the net pressure across the bed. The net pressure continues to drop during the hold subperiod and until it reaches a value $P_d$ below which the decreasing flow rate becomes insufficient to sustain fluidization, and the net pressure then tends to follow a more nearly linear response to the end of the cycle as the flow rate ramps down to zero.

During the cycle $50_d$ a function $F_d$ is generated, indicating that the material reaches fluidization at a lower net pressure than that reached during the cycle $50_c$. At a certain flow rate below the maximum rate in this cycle, the net pressure reaches the level $P_d$ and remains constant thereafter with increasing flow rate.

During a cycle $50_e$ a curve $F_e$ is generated, indicating that the material becomes and remains fluidized as soon as the net pressure reaches the level $P_d$, and the net pressure does not increase for greater values of the flow rate.

Observation of the curves generated by successive cycles as shown in FIG. 5 permits a determination of the duration of the test that is accurately repeatable for successive tests of the material. For example, a test may continue until the occurrence of three points 52 at the level $P_d$ in cycles $50_d$, $50_e$ and $50_f$. Thereupon, the test may be concluded by a ramp-down of the flow rate to zero in a final cycle $50_f$ in a predetermined subperiod 54.

It will be understood that the foregoing explanation of a representative test of material in connection with FIGS. 4 and 5 applies to a typical material that is relatively easy to fluidize without the formation of plugs of material or channeling, that is, the formation of channels of gas flow through the bed as opposed to uniform permeation of gas through the full cross section of the test chamber. However, the invention has distinct advantages for less easily fluidized materials.

Initially, with small flow rates, the material bed remains stationary, and the net pressure drop through the bed tends to remain more or less linear with increasing flow rate. Once the flow rate is sufficiently high to cause the force of the air flow upwards to balance the downward force of gravity, the material becomes fluidized. If the flow rate is increased above this value, it results either in expanding the fluidized bed and decreasing the bulk density, and/or the formation of bubbles in the bed. In general, a dense bed of material will exhibit a pressure drop more or less linear with increasing gas flow rates up to the point where it becomes fluidized, expands and is loosened, whereupon the pressure drop will decrease with increasing flow rate.

If the material is somewhat cohesive, it may tend to rise initially as a plug. Reducing or stopping air flow, as occurs in the practice of this invention, provides an opportunity for the plug to collapse. In the case of a plug forming, the pressure drop through the bed might exceed that calculated on the basis of the weight of material alone, as friction against the walls provides additional resistance. Once the plug breaks, subsequent refluidization will follow a different path.

Once fluidized, the material may begin to bubble. Slow, erratic bubbles may be responsible for scatter in the data forming the curves similar to FIG. 5, for example as bubbles get large enough to overcome cohesion.

On the other hand, if the material is sufficiently cohesive, it may not fluidize well, and the air or other gas might blow a channel through the material. Additional air flow through the diffuser 24 will not flow through the portion of the bed that is static, but instead will flow through the channel. In this case, the pressure drop obtained does not reach that based on the weight of material.

Similarly, even once material is fluidized, a flow channel may form, resulting in the collapse of a portion of the bed.

If there is a range of particle sizes within the material, it will not exhibit a distinct flow rate of initial fluidization. Instead, the finer portion might fluidize while the coarser portion remains stationary, in which case segregation is likely to have occurred. This results in a curved function instead of those shown in FIG. 5.

It is possible that the material is one that segregates slightly at low flow rates, with segregation becoming more intense at higher flow rates. This produces curves having corresponding characteristics.

From the foregoing description, it will be evident that an advantage of the invention resides in the ability to reach fluidization of the material. Simply increasing the flow rate from zero can result in channeling of the material. Problems arise with prior test methods in which this is overcome by increasing the flow rate to a very high value, then decreasing it back to a region of interest, in that they are not always effective, require higher flow rates than the test equipment can handle, and may cause significant material to be conveyed out of the test chamber. Vibration or impact to the chamber may pack the non-fluidized material further, making channeling more likely, and may induce other mechanisms of segregation. The present invention avoids the necessity of increasing the flow rates to values substantially above those required to achieve fluidization.

The present invention permits the design of test equipment for smaller volumes of sample material than those required for previous testers. With smaller test volumes, the invention provides a means for improved initiation of fluidization of the bed. The pulsing of air flow as described, with increasing peak flow rates for successive pulses, is an effective way of overcoming cohesion and channeling of the material.

The invention also uniquely addresses the critical goal of obtaining fluidization of the material at the lowest possible flow rate, in order to avoid elutriation of fines in the material, thus more closely mimicking the state of aeration of material experienced as a result of material transfer in production scale equipment. Observing curves corresponding to those of FIG. 5 for real time observation, test personnel learn for each pulse whether the material became fluidized, and if so, to some extent, whether segregation has fully developed. This allows the observer, or computational means, to be employed for minimally exceeding the flow rate necessary to achieve fluidization during a given material test.

EXAMPLE

A test chamber 16 mm in diameter was filled with a particulate material to a level of 95 mm. A five micron sintered metal diffuser disk 24 was fitted at the base of the chamber. A "target flow rate" was estimated, by prior test work and theoretical calculations, to be slightly above the lowest level sufficient to sustain fluidization. This target rate was divided by 7, the estimated number of cycles to complete the test, thus determining the increment of velocity Q/A to be added to each successive cycle.

Figure 6:
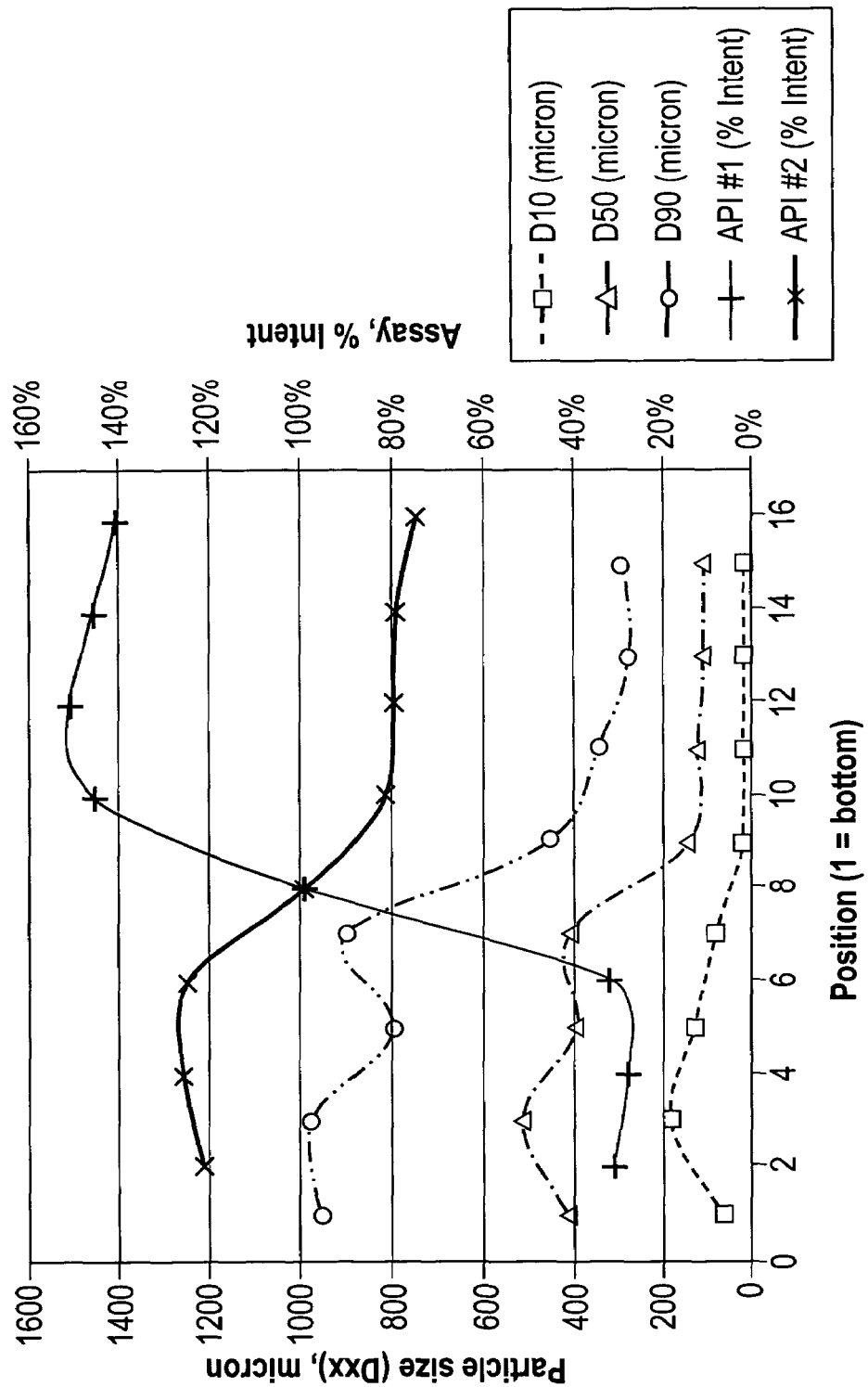
FIG. 6 shows the particle size and chemical assay results of a test on an example of material.

Upon completion of the test, sixteen 1.2 mil samples, each of which was located at a distinct level or position during the test, were successively recovered from the chamber. Even numbered samples were assayed for percent of intent and odd numbered samples were measured to determine particle size distribution. The results are illustrated in FIG. 6, and show that assay and particle size variations are pronounced, indicating possible segregation problems with this material.

FIGS. 7 to 11 illustrate details of the tester for practicing the test method of this invention. The sampling disk 26 permits removal of thin slices of the material from the bottom of the bed 30 each time the disk is rotated to present a succeeding recess 28 in the disk. As each recess in the disk is removed from the bed, the bed falls by gravity as a plug, filling the next recess. In some cases where the material is very cohesive, gas pressure may be applied to the top of the test chamber to ensure that each recess 28 is filled. In this way, the top-to-bottom composition of the bed is maintained as samples are collected. Generally, with a bed formed of coarse and fine particles, the initial samples are the coarsest and become progressively finer as the sampling disk rotates. In practice, about 16 samples may be collected, but the number of samples is variable according to choice. Once the samples are collected for each test, they can be analyzed by any known techniques of assay or other method of evaluation such as NIR ("Near-Infrared"), HPLC ("High Pressure Liquid Chromatography"), and AA ("Atomic Absorption"), particle size methods, microscopy, color, or bulk density.

The tester has a base assembly 60 which supports the test column 10 and a carrousel assembly 62. The base assembly supports a vertical test column shaft 64 comprising an outer clamp shaft 66 and an inner clamp shaft 68. A molded plastic bottom section 70 is slidably received over the shaft 64 and rests in a fixed position on the base 60. The sampling disk 26 is slidably received over the shaft 64 and rests on the bottom section 70. A central section 72, preferably of clear molded plastic with an elongate hole from top to bottom forming the test chamber 12, is slidably received over the shaft 64 and rests on the sampling disk 26. A top section 74 of molded plastic is slidably received over the shaft 64 and rests on the central section 72.

An outer shaft latch 76 fits within a recess in the top surface of the central section 72 and slides into a peripheral groove on the outer clamp shaft, whereby a downward force on the latter relative to the base 60 securely clamps together the central section 72, the sampling disk 26 and the bottom section 70. Similarly, an inner shaft latch 78 fits within a recess in the top surface of the top section 74 and slides into a peripheral groove on the inner clamp shaft 68, whereby a downward force on the latter relative to the base 30 securely clamps together the top section 74, the central section 72, the sampling disk 26 and the bottom section 70.

A clamping mechanism 80 is mounted in the base assembly 60 and provided with a clamping handle 82 (FIGS. 1 and 11) extending through an opening in the base and permitting movement of the handle to positions 82*a*, 82*b* and 82*c*. With the handle in position 82*a* the mechanism 80 applies downward force to the inner shaft 68 relative to the base, thereby clamping the top, central and bottom sections 74, 72 and 70 and the sampling disk 26 firmly together. With the handle in the position 82*b* the mechanism 80 exerts a downward force on the outer shaft but not the inner shaft, whereby the shaft latch 76 clamps together the central and bottom sections 72 and 70 with the sampling disk 26, leaving the top section 74 free to be rotated manually. With the handle in the position 82*c* neither the outer nor the inner shaft is subjected to a downward force, thereby allowing the central and top sections as well as the sampling disk 26 to be manually rotated as desired.

The sampling disk 26 has notches 84 (FIG. 11) spaced 90 degrees around its periphery and fits within a ring 86 bearing a ratchet pawl 88 with a handle 90 for advancing the sampling disk in successive movements of 90 degrees.

Figure 10:
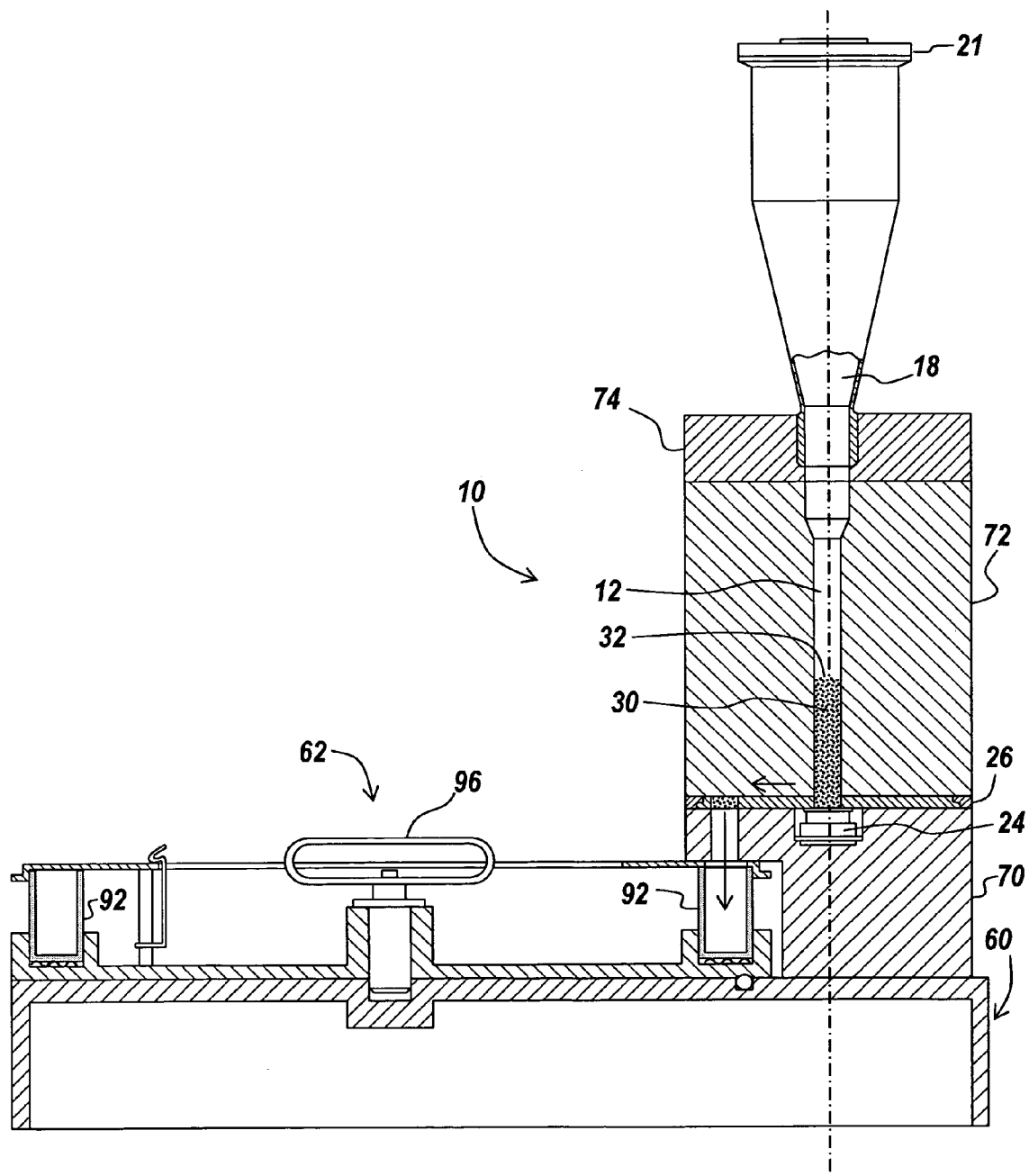
FIG. 10 is an elevation in section of the tester taken on line 10-10 of FIG. 1 showing details of the discharge of tested material to the sample vials.
Figure 11:
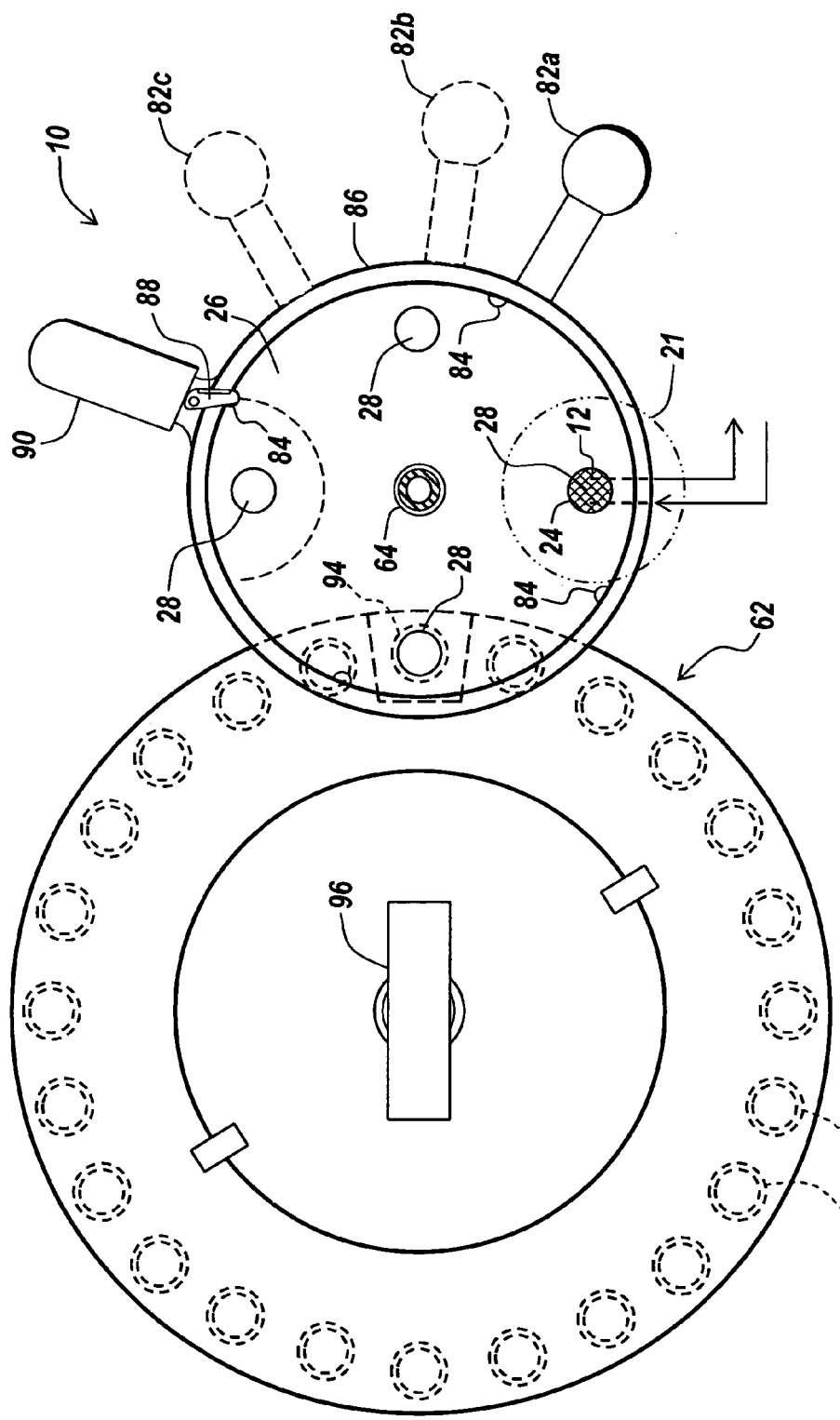
FIG. 11 is a view in plan of the tester taken on line 11-11 of FIG. 1 and corresponding to FIG. 10.

The carrousel 62 is provided with recesses for receiving a number of vials 92 (FIG. 10). A suitable mechanism is provided for manually advancing the carrousel to present successive vials in a position 94 (FIG. 11) for receiving the samples. A suitable handle 96 is provided for clamping the carrousel to the base 60 and for carrying the carrousel with filled vials to a separate location for assays or other measurements.

Figure 7:
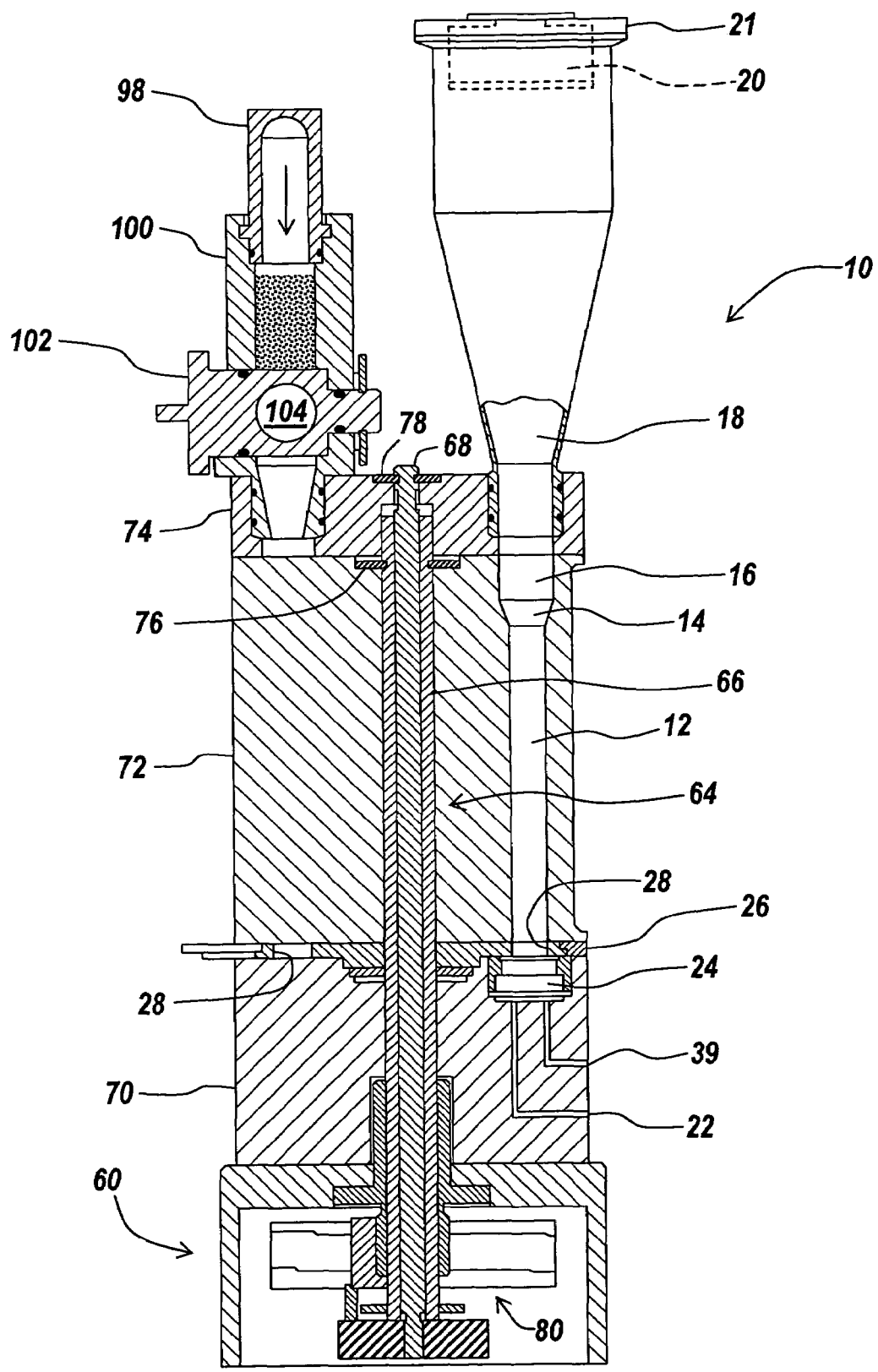
FIG. 7 is an elevation in section of the tester taken on line 7-7 of FIG. 1 showing the loading of a fill capsule of test material.
Figure 8:
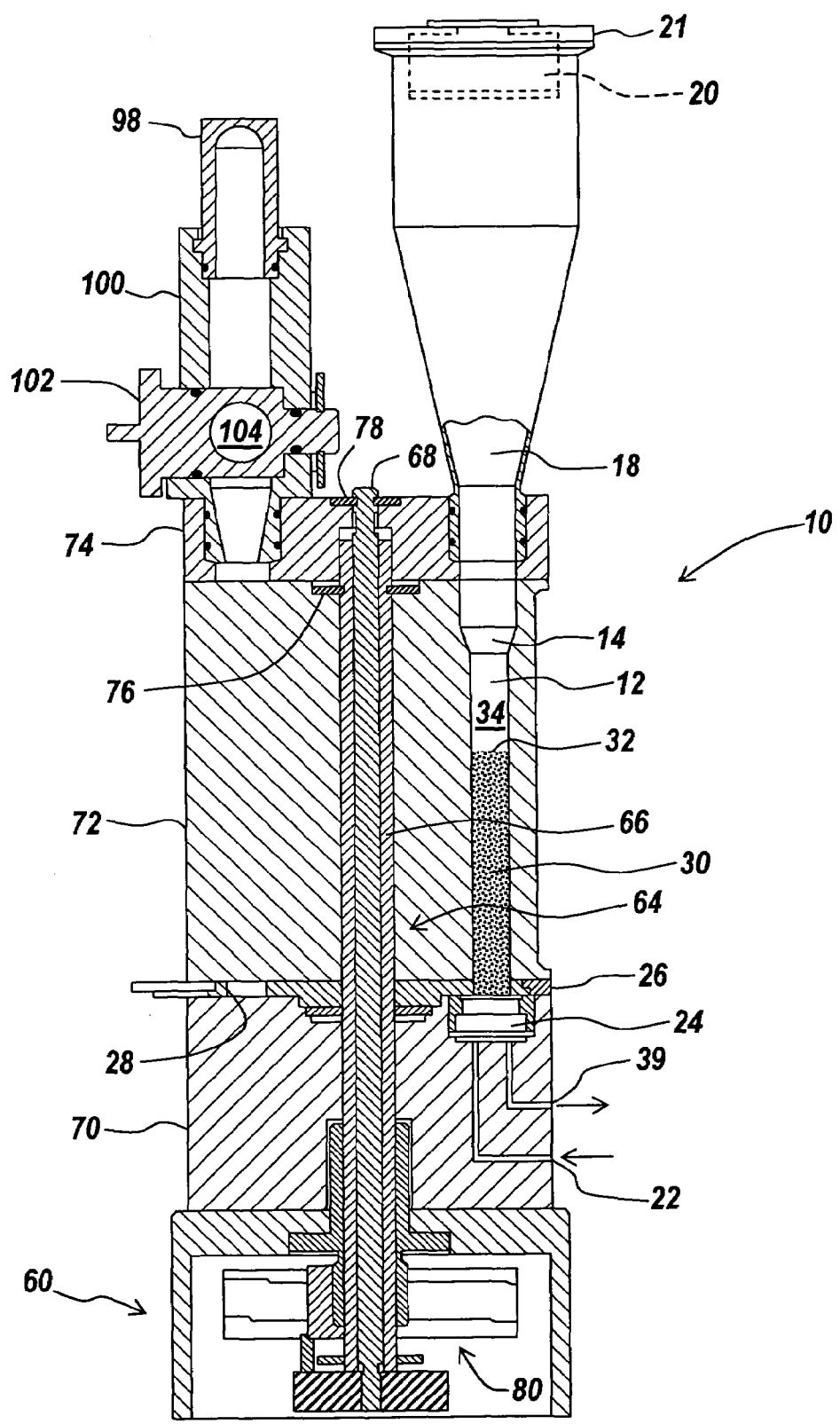
FIG. 8 is an elevation similar to FIG. 7 showing a loaded bed of the material in position for running a test.
Figure 9:
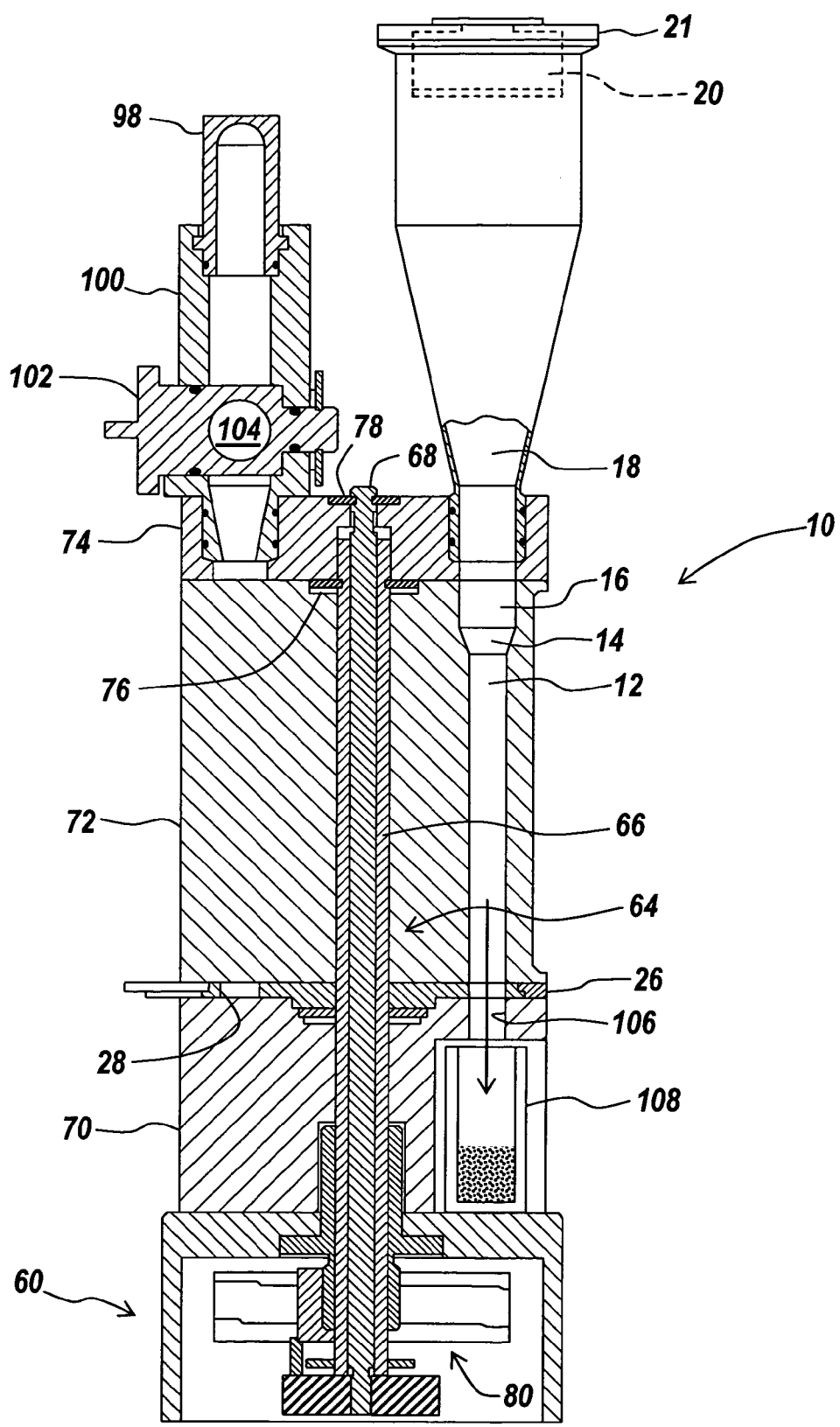
FIG. 9 is an elevation similar to FIG. 7 showing the tester in position to abort a test and discharge the test column.

Material to be tested is initially loaded into a fill module 98 when held in a position inverted from that shown in FIGS. 7 to 9. An inlet valve body 100 having a stopcock 102 is then attached to the top of the module 98. The stopcock has a thru hole 104. With the valve in the closed position as shown, the module and valve subassembly can be inserted into an aperture in the top section 74 diametrically opposed to an aperture for receiving the elutriation chamber 18.

FIG. 7 shows the test column 10 in position for the start of a test with the fill module and inlet valve body fitted on the top section 74, and with the test chamber 12 aligned with the elutriation chamber 18, a recess 28 in the sampling disk 26 and the diffuser 24. With the clamping handle 82 moved to the position 82*b* (FIG. 11) the top section 74 is rotated 180 degrees into alignment with the test chamber 12, and the stopcock is turned to permit the test material to fall into the chamber 12. The top section is then rotated to its original position as shown in FIG. 8. The clamping handle 82 is then moved to the position 82*a*. The test procedure may then be commenced as described above.

When the test is completed the clamping handle 82 is moved to the position 82*c*, thereby removing pressure from the sampling disk and permitting it to be rotated sequentially while the bottom, central and top sections of the test column remain fixed, to remove successive slices of the tested material from the chamber 12, depositing them sequentially in the sample vials 92.

If it is desired to abort a test procedure before completion, with the clamping handle in the position 82*c* the central section 72 can be manually rotated to a position illustrated in FIG. 9. In this position the chamber 12 is aligned with an aperture 28 in the sampling disk and a hole 106 in the bottom section 70 opening into a recess in the bottom section in which a receptacle 108 is placed.

The invention claimed is:

1. The method of fluidizing a bed of particulate solids for causing a segregation effect, including the steps of
   loading the bed into a test chamber, and
   causing a stream of fluidizing gas to flow through an inlet into the test chamber while controlling the rate of flow in a series of consecutive cycles of the flow rate while measuring the gas pressure at the inlet and recording a function of said pressure and flow rate, said rate in each cycle increasing to a maximum and then decreasing to a rate insufficient to sustain fluidization of the material, the maximum rate increasing from each cycle to the next succeeding cycle, the maximum rate in the initial cycle being less than that which causes fluidization of the material, the maximum rate in the final cycle being at least sufficient to cause fluidization of the material.

2. The method of claim 1, in which said maximum rate is increased by a predetermined increment in successive cycles.

3. The method of claim 2, in which said increment is constant for a plurality of cycles.

4. The method of claim 1, in which said rate is decreased substantially to zero in each cycle.

5. The method of claim 1, including the preliminary steps of causing a stream of fluidizing gas to flow at an increasing rate through said inlet into the unloaded test chamber, and measuring and recording in a memory a background gas pressure at the inlet corresponding to each last mentioned rate, said function being the difference between the measured inlet gas pressure with the chamber loaded and the background gas pressure recorded in the memory for the corresponding flow rate.

6. The method of claim 1, in which the cycles are repeated until said function reaches the same maximum level for a predetermined number of cycles.

7. The method of claim 6, in which the cycles each comprise a ramp-up period of increasing rate of gas flow, a hold period of constant maximum rate of gas flow, and a ramp-down period of decreasing rate of gas flow, corresponding periods in each cycle being of predetermined duration.

8. The method of claim 7, including the step of decreasing the rate of gas flow to zero in a final ramp-down period of the cycle in which said function has reached the same maximum level for said predetermined number of cycles.

9. The method of claim 1, in which the cycles each comprise a ramp-up period of increasing rate of gas flow, a hold period of constant maximum rate of gas flow, and a ramp-down period of decreasing rate of gas flow, corresponding periods in each cycle being of predetermined duration.

* * * * *